(12) United States Patent
Sullivan et al.

(10) Patent No.: US 8,798,736 B2
(45) Date of Patent: *Aug. 5, 2014

(54) EEG CONTROL OF DEVICES USING SENSORY EVOKED POTENTIALS

(75) Inventors: Tom Sullivan, San Jose, CA (US); Arnaud Delorme, San Diego, CA (US); An Luo, San Jose, CA (US)

(73) Assignee: NeuroSky, Inc., San Jose, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/408,028

(22) Filed: Feb. 29, 2012

(65) Prior Publication Data

US 2012/0220889 A1 Aug. 30, 2012

Related U.S. Application Data

(63) Continuation of application No. 12/381,887, filed on Mar. 16, 2009, now Pat. No. 8,155,736.

(51) Int. Cl.
*A61B 5/04* (2006.01)

(52) U.S. Cl.
USPC ........................................... 600/544

(58) Field of Classification Search
USPC ................................. 600/544, 545
See application file for complete search history.

(56) References Cited

U.S. PATENT DOCUMENTS

| 4,493,327 | A | * | 1/1985 | Bergelson et al. | 600/544 |
| 4,926,969 | A | * | 5/1990 | Wright et al. | 600/544 |
| 5,052,401 | A | * | 10/1991 | Sherwin | 600/558 |
| 5,638,825 | A | | 6/1997 | Yamazaki et al. | |
| 5,687,291 | A | | 11/1997 | Smyth | |
| 6,092,058 | A | | 7/2000 | Smyth | |
| 8,374,687 | B2 | * | 2/2013 | Mathan et al. | 600/544 |
| 2005/0085744 | A1 | | 4/2005 | Beverina et al. | |
| 2008/0208072 | A1 | * | 8/2008 | Fadem et al. | 600/544 |
| 2009/0187114 | A1 | | 7/2009 | Morikawa et al. | |
| 2009/0247895 | A1 | | 10/2009 | Morikawa et al. | |
| 2010/0106042 | A1 | | 4/2010 | Morikawa et al. | |
| 2010/0109859 | A1 | | 5/2010 | Lakosky | |
| 2011/0289030 | A1 | | 11/2011 | Lu et al. | |

FOREIGN PATENT DOCUMENTS

| CN | 101273887 | 5/2008 |
| JP | 5178592 | 7/1976 |
| JP | 3297443 | 12/1991 |
| JP | 2002166050 | 6/2002 |
| WO | 95/18565 | 7/1995 |
| WO | 99/09539 | 2/1999 |
| WO | 2004100766 | 11/2004 |

OTHER PUBLICATIONS

Grant McMillan, Cseriac Gateway, Brain-Actuated Control: Thinking Ahead to "Firefox", Magazine, vol. VI, No. 5 (1995), Report Date Apr. 1996, pp. 8-9.

* cited by examiner

*Primary Examiner* — Navin Natnithithadha
*Assistant Examiner* — Etsub Berhanu
(74) *Attorney, Agent, or Firm* — Van Pelt, Yi & James LLP

(57) ABSTRACT

An EEG control of devices using Sensory Evoked Potentials (SEPs) (e.g., visually-evoked potentials), is disclosed. In some embodiments, a system receives a plurality of EEG signal samples; generates a stimulus locked average signal using the plurality of EEG signal samples; and determines whether the plurality of EEG signal samples are evoked in response to a pattern of stimulus.

16 Claims, 18 Drawing Sheets

EEG CONTROL OF DEVICES USING SENSORY EVOKED POTENTIALS

CROSS REFERENCE TO OTHER APPLICATIONS

This application is a continuation of co-pending U.S. patent application Ser. No. 12/381,887 entitled EEG CONTROL OF DEVICES USING SENSORY EVOKED POTENTIALS filed Mar. 16, 2009 which is incorporated herein by reference for all purposes.

BACKGROUND OF THE INVENTION

EEG detection systems exist that include bio-signal sensors (e.g., electroencephalography (EEG) sensors) that allow brain waves of a user to be measured. Sensory Evoked Potentials (SEPs) are generally involuntary EEG signals of a person generated when the person responds to a stimulus (e.g., visually-evoked potentials, or EEG potentials evoked through other senses, such as tactile-evoked or audio-evoked potential). Thus, it is desirable to provide EEG detection systems that can be used for SEP applications and/or EEG control of devices using SEPs, such as visually-evoked potentials.

BRIEF DESCRIPTION OF THE DRAWINGS

Various embodiments of the invention are disclosed in the following detailed description and the accompanying drawings.

DETAILED DESCRIPTION

Figure 1:
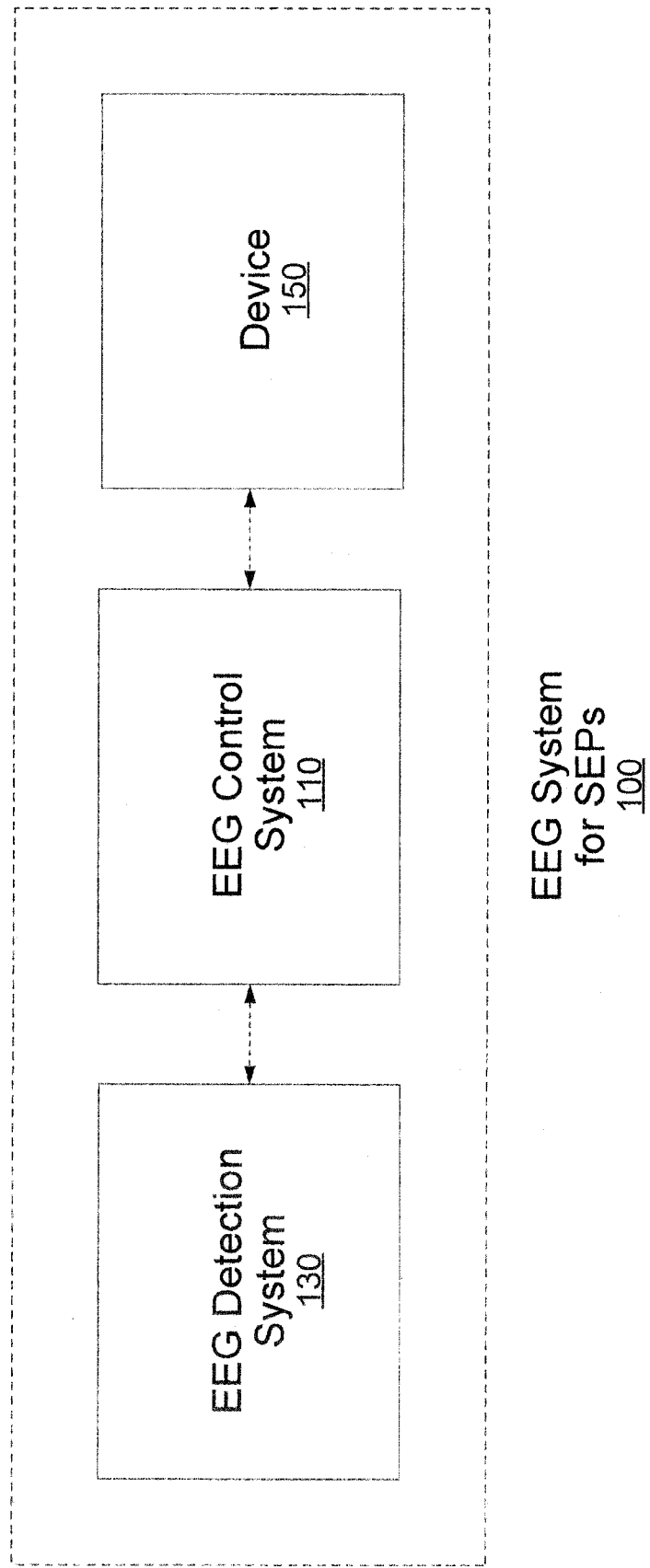
FIG. 1 is a block diagram illustrating an EEG system for SEPs in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits (e.g., PCBs, ASICs, and/or FPGAs), and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The typical electroencephalography (EEG) signal that is generated from a stimulus event, such as the user looking at a flashing light, is a relatively weak signal. As a result, it is not easy to detect such signals with the typical amount of noise (e.g., from the circuit, external sources, and/or non-relevant EEG sources) in the detected signal (e.g., using dry, contact sensor(s), wet, contact sensor(s), or non-contact EEG sensor(s)). In addition, it is also not easy to detect the signature EEG signal in a timely manner (e.g., within 2 to 3 seconds). For example, systems that use lights that flash at fixed frequencies rely on monitoring EEG signals for an increase in power at the light frequencies. These systems and methods are generally referred to as steady-state visually-evoked potentials (SS-VEPs). However, power estimation techniques (e.g., FFT techniques) are not reliable when the level of noise in the EEG signal is of the same order as the signal that is being estimated, which is often the case, especially with non-contact EEG sensors.

Techniques that rely on EEG potentials generated by thoughts or high-level perceptions are slow. For example, with P300 event-related potentials (ERPs), the user must recognize relatively rare events requiring that events be spaced relatively far apart in time (e.g., ten events will be spaced over one minute), which limits the speed at which a determination/action can be performed with EEG-based control.

Accordingly, a system and method that can efficiently and effectively determine stimulus evoked events (e.g., SEPs, such as visually-evoked potentials) based on EEG signals is needed.

In some embodiments, a system is provided that efficiently and effectively identifies EEG signals associated with SEPs to control a device. In some embodiments, a system is provided that uses flashing lights (e.g., from one or more light-emitting diodes (LEDs) and/or from a computer screen or television (TV) screen) that correspond to commands to/from a user. In some embodiments, the flashing lights in the system flash at distinct fixed frequencies. In some embodiments, the flashing lights in the system flash at variable frequencies in a fixed pattern or in non-periodic frequencies. The system records detected EEG signals of the user and determines whether/when a user is looking at one of the flashing lights. As used herein, SEPs generally refer to involuntary EEG signals generated when the user is exposed to (e.g., rapidly) repeating sensory stimuli (e.g., visual, such as a flashing light or another involuntary response to a visual stimulus event, audio, tactile, or other stimulus event). As used herein, SEPs do not include events based on a user's thought and higher level perceptions (e.g., recognition of a relatively rare event, like P300s, or recognition of a grammar mistake), which generally occur after a longer period of time offset (and generally require a relatively slow repetition of such events so that the small EEG signal samples can be added and averaged for identification purposes), and which are generally referred to as event-related potentials (ERPs).

Figure 18:
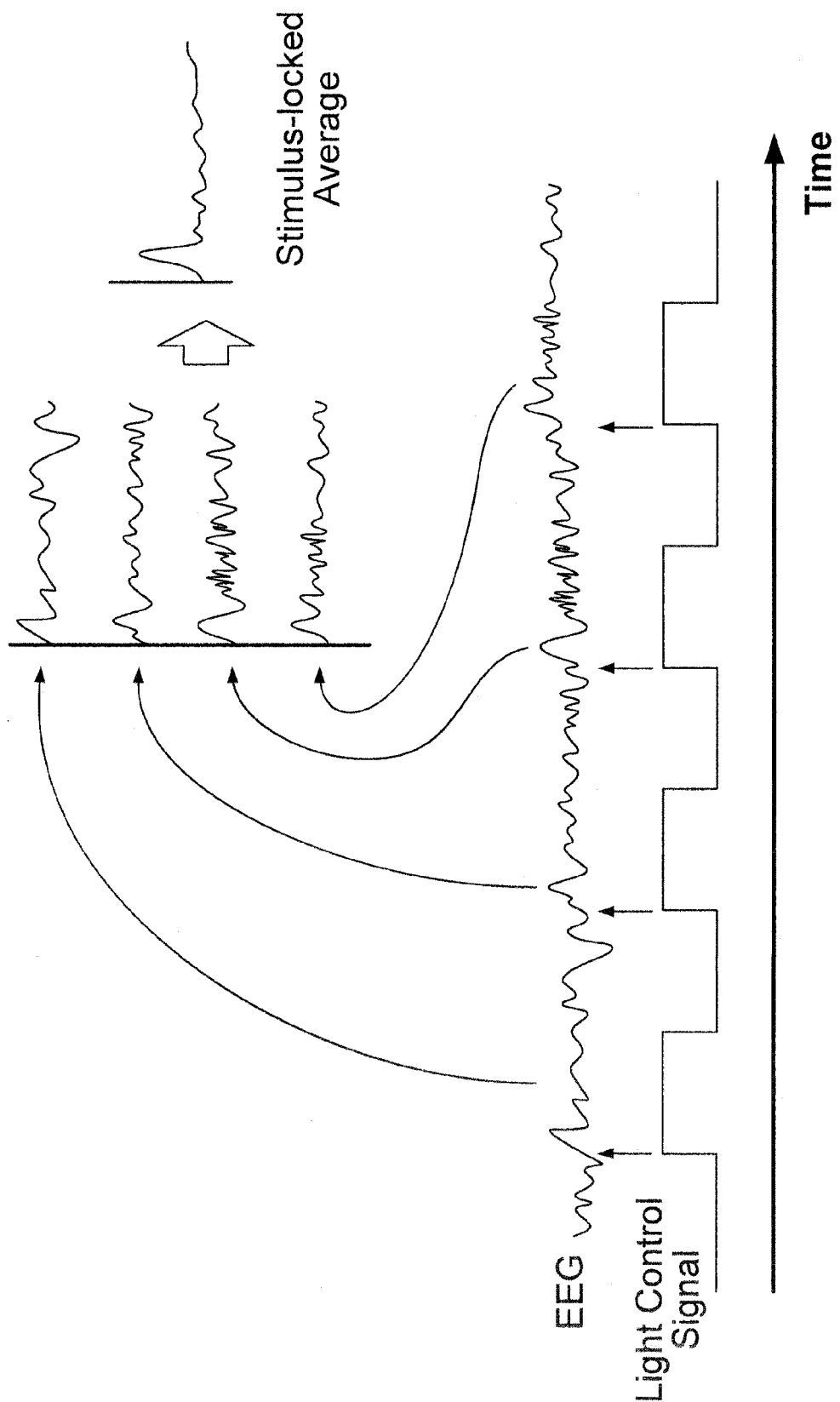
FIG. 18 is a chart illustrating an example for generating a flash-locked average signal in accordance with some embodiments.

In some embodiments, a system is provided that uses various signal averaging techniques on SEP signals generated in response to rapidly repeating sensory stimuli. In some embodiments, such as shown in FIG. 18, an EEG signal from a user reacting to a rapidly repeated stimulus event, such as the user looking at a flashing light, and a signal that is used to control the stimulus are both measured. For example, segments of the EEG signal of a fixed length (e.g., 100 milliseconds (ms)) that follow the light onsets are first recorded. The recorded data is then averaged together such that the first EEG data points following stimulus onsets are averaged together, then all the second data points that follow stimulus onsets are averaged together, then the third data points that follow stimulus onsets are averaged together, and so forth. The result provides a stimulus-locked average signal (or in this example, a flash-locked average signal) with an averaged waveform of the same length as the recorded segments. For example, if the user looked at the light, then the averaged waveform will include a characteristic shape (e.g., a positive deflection in EEG voltage about 30 ms after the light onset time). This characteristic shape of the averaged waveform can be detected in a variety of ways as further described herein. If the user did not look at the light the averaged waveform will be mostly flat.

Figure 17:
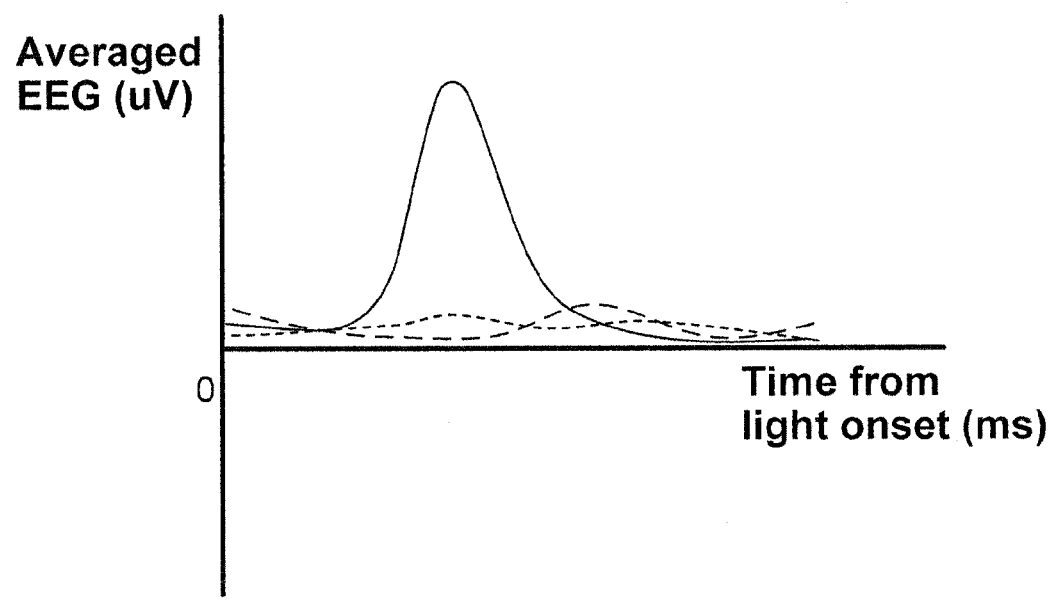
FIG. 17 is a chart illustrating an example of four stimulus-locked averages in accordance with some embodiments.

In some embodiments, the system includes more than one stimuli. For example, FIG. 17 is a chart illustrating an example of four stimulus-locked averages. One of the averages has developed a characteristic shape, whereas, the other averages are relatively flat.

The characteristic shape can be detected using various techniques including comparing to a threshold at some delay from the onset, integrating the averaged EEG signal over some time period and comparing that result to a threshold, or creating a classifier that distinguishes if the light is being attended. As another example, a prototype of an ideal average (e.g., when a light is being attended) can be constructed and multiplied by the actual average. A high value result will indicate an attended light. The prototype can be constructed in a variety of ways, including computing EEG averages when a user is known to be looking at the light, or constructing an auto-regression model of EEG data when a user is known to be looking at the light, and using the coefficients of that auto-regression model as the data elements of the prototype.

In some embodiments, the system is used to control devices using certain EEG signals that are evoked by a user looking at flashing lights. For example, a control signal can also be provided to another device (e.g., an entertainment system, an educational system, a medical system, an application for automobiles, and a computer executing an application) based on detected SEPs. For example, the system can include several flashing lights that each represent a command that is used to control the device. When a user looks at one of the flashing lights, a unique signature in the EEG signal can be determined to be present in the user's recorded EEG signals pattern using stimulus-locked average techniques. For example, a computing device (e.g., a programmed computer/laptop/netbook/portable computing device, microcontroller, ASIC, and/or FPGA) can perform an efficient and effective algorithm (e.g., classifier) that continuously checks for unique EEG signal signatures that correspond to each flashing light. In some embodiments, the algorithm performs such determinations in real-time (e.g., computes such determinations within about 3 seconds of the event, in this case, the flashing light(s) event(s)). In some embodiments, various parameters are adjusted to maximize the EEG signal and increase the visually-evoked potential detection rate, such as light brightness, color, spacing, frequency, duty cycle, and the amount of visual field that is used by the lights. When a visually-evoked potential is detected, then the corresponding command is sent to the controlled device.

For example, the device that is controlled can be a toy, and when the system recognizes that one of the flashing lights is being looked at by the user, then something fun happens with the toy (e.g., based on a command from the system for detecting SEPs). As another example, objects within a video game can flash, and the game can recognize what the user is looking at (e.g., which flashing object) and incorporate that into the game play. As another example, objects within a flight simulator or a military or other application can flash, and the game can recognize what the user is looking at (e.g., which flashing object) and incorporate that into the application. As another example, the device that is controlled can be a programmed computer, or any apparatus, that allows a user who cannot use their hands, but needs the ability to make a system selection. As another example, the device that is controlled can be an automobile application, in which a selection or setting for an automobile interface for drivers and/or passengers. For example, the EEG detection system can be in the form of a cap worn by the user and/or integrated into a headrest of an automobile seat, and blinking/flashing lights can be integrated into a console/dashboard of the automobile for controlling radio, temperature, or other controls/settings, or combined with various other EEG applications for automobiles or other devices, such as a mental state monitor (e.g., for determining attention, anxiety, surprise, and/or drowsy states, such as for a driver of the automobile, an airplane, or any other device).

FIG. 1 is a block diagram illustrating an EEG system for SEPs in accordance with some embodiments. As shown, an EEG system for SEPs 100 includes an EEG control system 110, an EEG detection system 130, and a device 150. In some embodiments, the device 150 is controlled by the EEG control system 110. In some embodiments, the device 150 is included with or integrated with the EEG system for SEPs, as shown, and communicates with the device 150 using a serial or other communication channel. In some embodiments, the device 150 is separate from the EEG system for SEPs 100 and is in communication with the EEG control system 110 using a wired line or wireless communication. In some embodiments, the EEG control system 110 communicates with the EEG detection system 130 using a serial or other communication channel (e.g., wired or wireless).

In some embodiments, the EEG detection system 130 detects EEG signals of a user, and the EEG control system 110 includes a processor configured to perform an SEP determination algorithm (e.g., a real-time classification algorithm/classifier) for EEG signals detected by EEG detection system 130. In some embodiments, various SEP determination techniques are used (e.g., time domain SEP determination algorithms/classifiers), as disclosed herein.

In some embodiments, based on the SEP determination(s), the EEG control system 110 sends corresponding control signal(s) to the device 150 (e.g., based on associated SEPs). In some embodiments, the EEG detection system 130 sends raw EEG signal data, or in some embodiments processed EEG signal data (e.g., to filter out noise), to the EEG control system 110.

Figure 2:
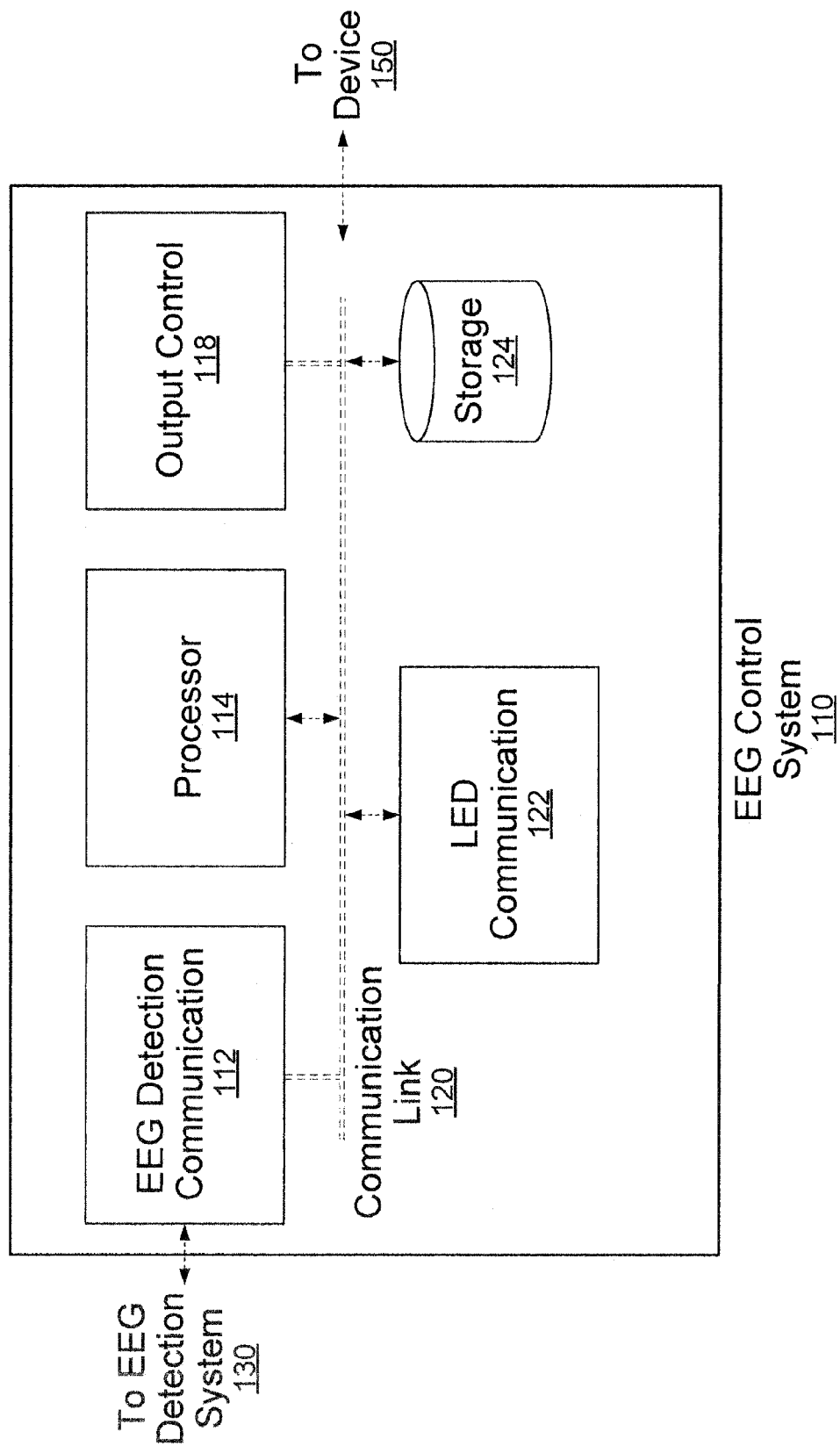
FIG. 2 is a functional diagram illustrating an EEG control system in accordance with some embodiments.

FIG. 2 is a functional diagram illustrating an EEG control system in accordance with some embodiments. As shown, the EEG control system 130 includes an EEG detection communication component 112 for communicating with the EEG detection system 130, a processor 114 for performing an SEP determination algorithm for EEG signals detected by EEG detection system 130, an output control 118 for communicating with the device 150, LED communication 122 for communicating with one or more LEDs (e.g., a flashing LED lights system), and a data storage 124 (e.g., for storing received EEG signal samples and associated timing data, such as for the flashing LED lights), and a communication link 120.

In some embodiments, a programmed computer is in communication with the EEG control system 110, and the EEG control system 110 also includes an EEG data to computer component for sending detected EEG signal samples to the computer. In this example, the computer includes a processor configured to perform an SEP determination algorithm for EEG signals detected by EEG detection system 130, and the computer can then provide the results of the analysis to the EEG control system for controlling the device (e.g., based on associated SEPs). In some embodiments, the computer includes a processor configured to perform an SEP determination algorithm for EEG signals detected by EEG detection system 130, and the computer sends corresponding control signal(s) to the device based on the results of the analysis of the EEG signal samples. In some embodiments, all or just a portion of the analysis of the EEG signal samples is performed by the programmed computer. In some embodiments, all or just a portion of the analysis of the EEG signal samples is performed in an EEG detection system (e.g., an ASIC integrated with or in communication with EEG sensors).

Figure 3:
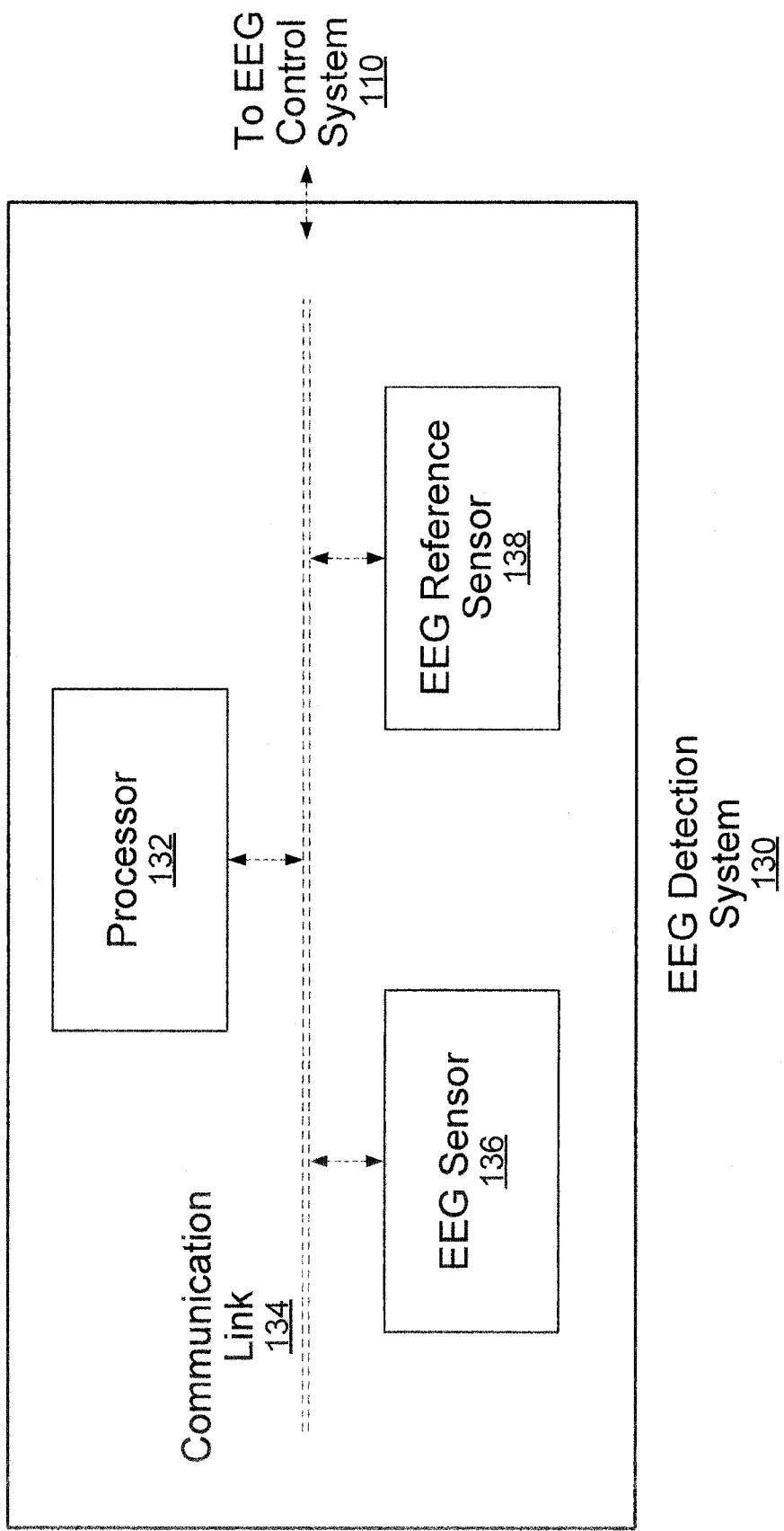
FIG. 3 is a functional diagram illustrating an EEG detection system in accordance with some embodiments.

FIG. 3 is a functional diagram illustrating an EEG detection system in accordance with some embodiments. As shown, the EEG detection system 130 includes a processor 132 (e.g., an FPGA or ASIC), active EEG sensor 136, and a reference EEG sensor 138, and a communication link 134. The measured EEG signals are provided to the EEG control system 110. In some embodiments, a continuous measure of EEG signal samples are detected and provided to the EEG control system 110.

Figure 4:
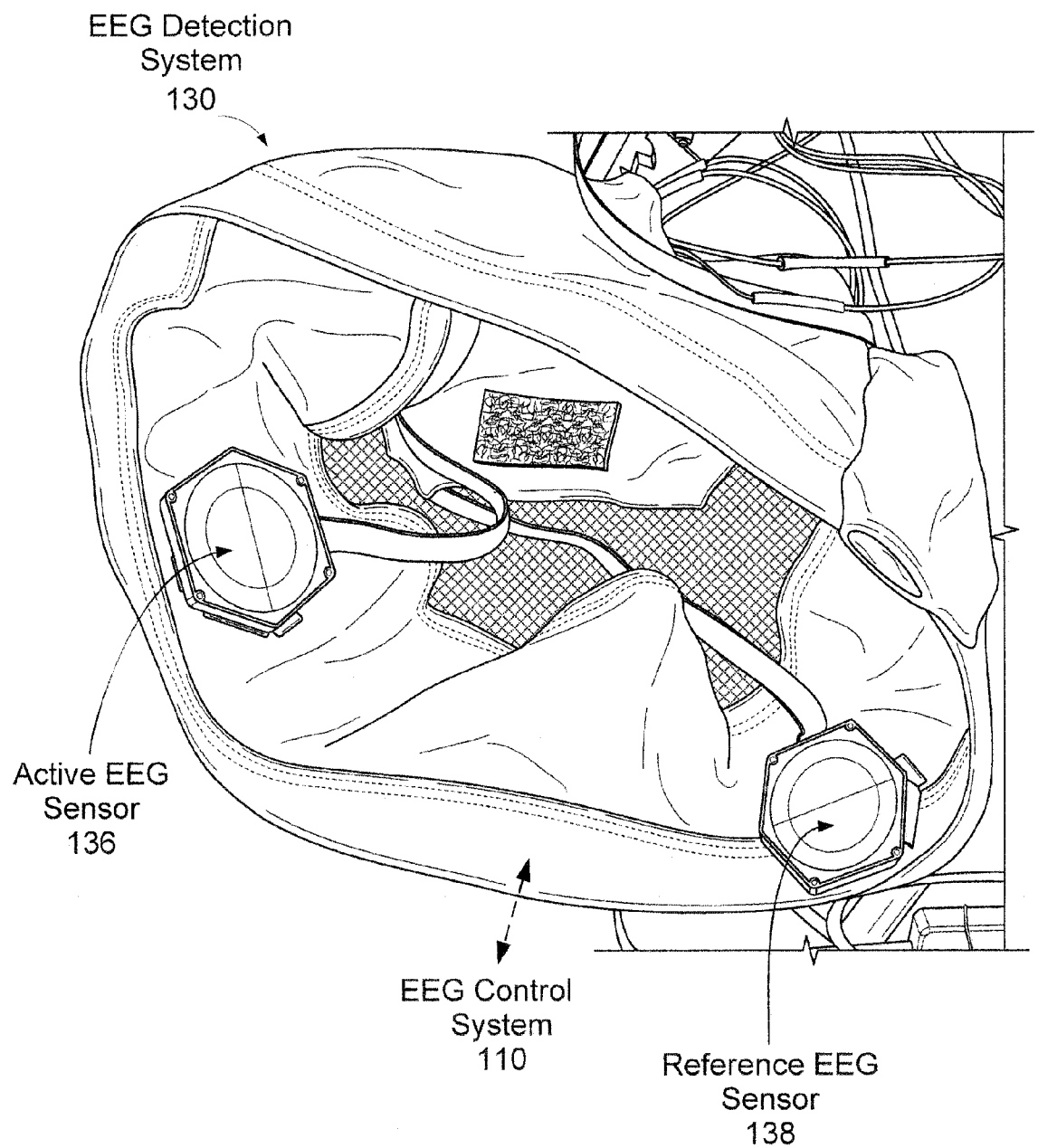
FIG. 4 illustrates an EEG detection system including an EEG sensor and reference EEG sensor mounted inside a hat in accordance with some embodiments.

FIG. 4 illustrates an EEG detection system including an EEG sensor and reference EEG sensor mounted inside a hat in accordance with some embodiments. As shown, the EEG detection system 130 is a hat to be worn by the user that includes the EEG sensor 136 and the reference EEG sensor 138 inside the hat. The EEG sensor 136 and the reference EEG sensor 138 are connected via a wired line communication (e.g., serial communication link) to the EEG control system 110. In some embodiments, the EEG sensor 136 is located inside the hat to be on the occipital region of the user's head (e.g., for visual event related EEG signal detection) when the hat is worn by the user, and the reference EEG sensor 138 is located in another location on the user's head (e.g., on the forehead, a side of the user's head above an ear, or on the back of the user's head in a location different than the location of the active EEG sensor). In some embodiments, the EEG sensor(s) are located in different locations based on the type of stimulus events to be detected as will be appreciated by those of ordinary skill in the art. In some embodiments, the EEG sensor 136 and reference EEG sensor 138 are non-contact EEG sensors. In some embodiments, the EEG detection system includes more than one EEG sensor 136. In some embodiments, the EEG detection system 130 is in the form of a headset, audio headset, an automobile seat headrest, or any other form of apparatus or module that can be used by the user to securely locate the EEG sensor(s) 136 and the reference EEG sensor 138 on appropriate locations of the user's head for EEG signal detection. In some embodiments, the EEG detection system 130 (e.g., a hat/cap, as shown) includes a grounded ear clip to reduce the amount of noise.

Figure 5B:
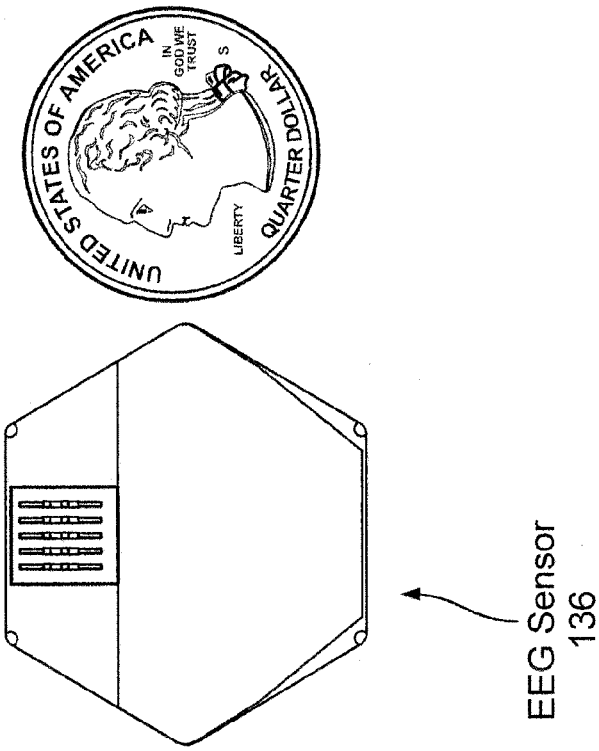
FIGS. 5A-B illustrate EEG sensors in accordance with some embodiments.
Figure 5A:
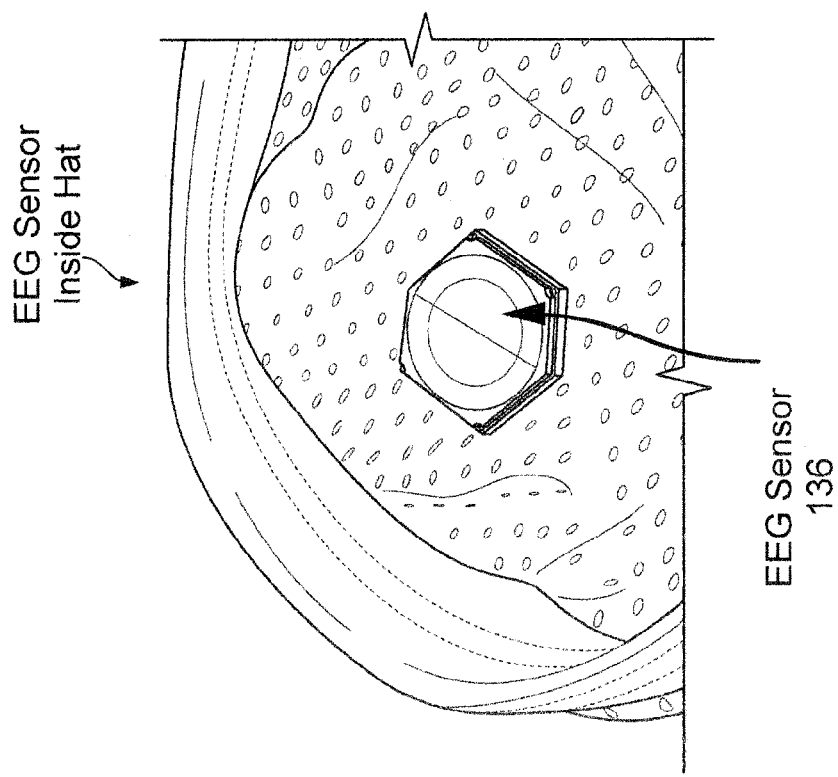

FIGS. 5A-B illustrate EEG sensors in accordance with some embodiments. As shown in FIG. 5A, the EEG sensor 136 is mounted on the inside of the EEG signal detection hat. As shown in FIG. 5B, a top-side of the EEG sensor 136 is illustrated, in which the illustrated EEG sensor 136 is a non-contact electrode that is approximately the size of a U.S. quarter coin. The EEG sensor 136 is integrated into a printed circuit board (PCB) with analog front-end circuitry that amplifies the EEG signal and filters out noise. The EEG sensor 136 includes a metal shield, which protects, for example, the sensitive signal from external noise. In some embodiments, the circuitry for the EEG sensor 136 is integrated into an ASIC.

Figure 6:
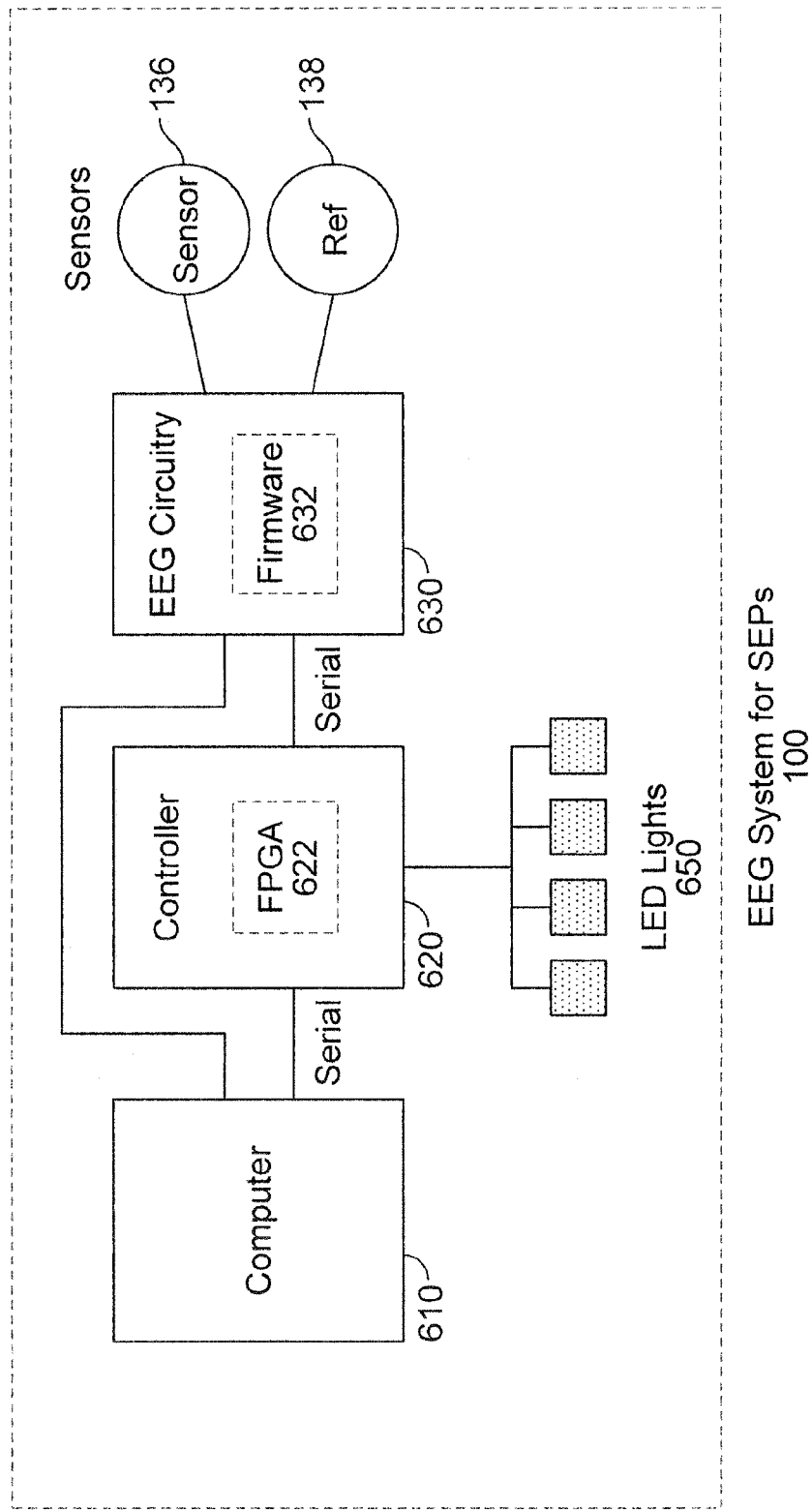
FIG. 6 is another block diagram illustrating an EEG system for SEPs in accordance with some embodiments.

FIG. 6 is another block diagram illustrating an EEG system for SEPs in accordance with some embodiments. As shown, the EEG system for SEPs 100 includes a computer 610 configured (e.g., programmed) to perform an SEP determination algorithm for detected EEG signals, a controller 620 for controlling LED (flashing) lights system 650 (e.g., controlling the timing of onsets and offsets of light flashes and which lights flash in which patterns), and EEG circuitry 630 for receiving (and in some embodiments, processing) detected EEG signals from the EEG sensor 136 and the reference EEG sensor 138. As shown, four LED lights are provided in the LED lights system 650. In some embodiments, one or more LED lights are provided.

The controller 620 also includes an FPGA 622 (or, in some embodiments, any other form of a processor or software executed on a processor, such as an ASIC or programmed processor). In some embodiments, the controller 620 controls the LED lights 650 and also communicates with the computer 610 and the EEG circuitry 630. In some embodiments, the controller 620 controls the flashing lights and receives EEG signal (sample) data from the EEG circuitry 630. In some embodiments, the controller also combines the received EEG signal data and light timing data (e.g., for the flashing onsets/offsets of the LED lights system 650) into a serial stream that is sent to the computer 610 for further analysis and processing (e.g., using a real-time SEP determination algorithm). In some embodiments, the controller 620 also sends control signals to a controlled device (e.g., the device 150).

The EEG circuitry 630 includes firmware 632 (or, in some embodiments, any other form of a processor or software executed on a processor, such as an ASIC or FPGA or programmed processor). The controller is in serial communication with the computer 610 and the EEG circuitry 630, as shown. In some embodiments, the EEG circuitry 630 is also directly connected to, as shown via a direct serial connection (or, in some embodiments, in direct communication, wired or wireless) with the computer 610. In some embodiments, one or more of these connections are wireless.

Figure 7:
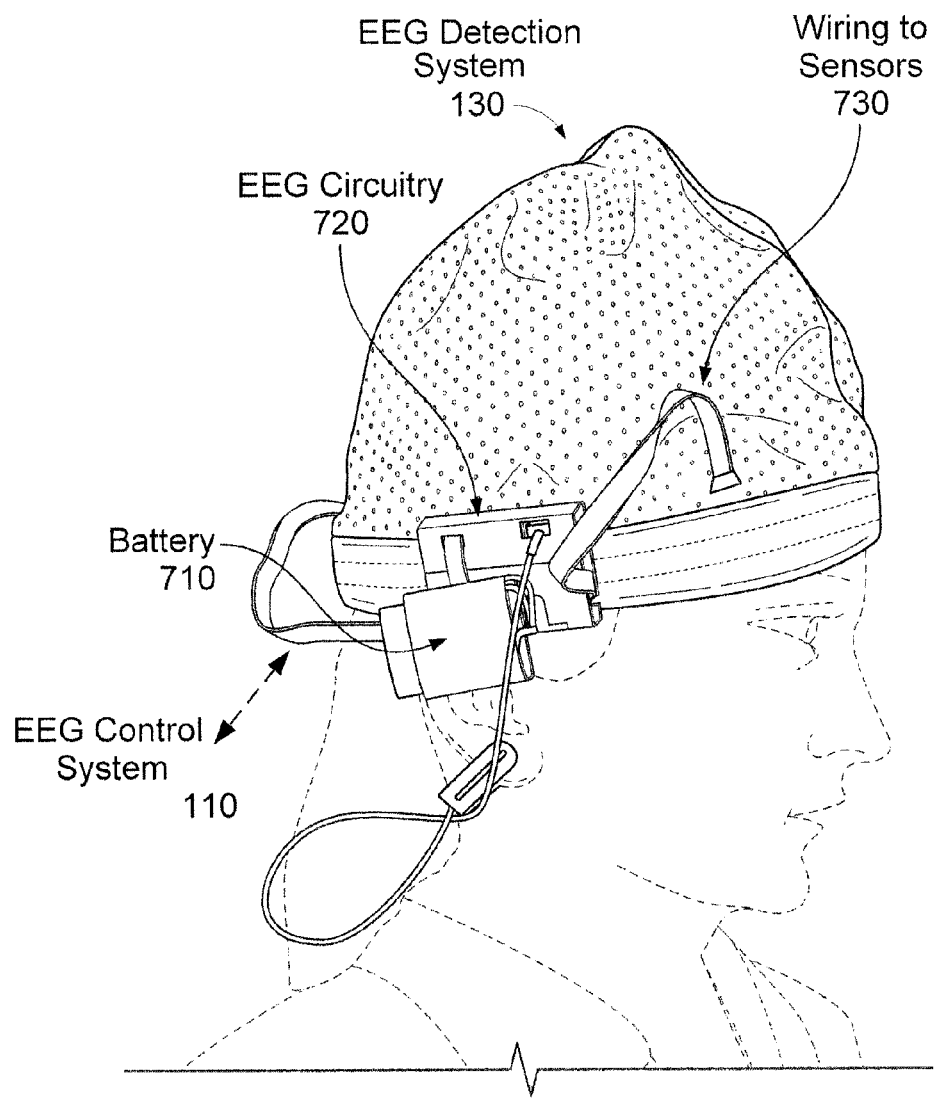
FIG. 7 illustrates an EEG detection system with non-contact EEG sensors in accordance with some embodiments.

FIG. 7 illustrates an EEG detection system with non-contact EEG sensors in accordance with some embodiments. As shown, the EEG detection system 130 is in the form of a hat or cap worn by the user, which includes a battery 710 (e.g., a rechargeable lithium ion battery), EEG circuitry 720, and wiring to the EEG sensors 730 (the non-contact EEG sensors are mounted inside of the hat and, thus, not visible in this depiction of the hat being worn by the user). In some embodiments, the EEG detection system 130 is in wireless (e.g., Bluetooth or another wireless protocol) with other apparatus/devices, such as the EEG control system 110. In some embodiments, the battery 710, EEG circuitry 720, and wiring to the EEG sensors 730 are more tightly integrated into the hat/cap and/or other head wear apparatus (as similarly discussed above), and, in some embodiments, generally not visible when worn by the user. As will be appreciated, various other designs and head wear apparatus can be used to provide the EEG detection system 130 disclosed herein.

Figure 8B:
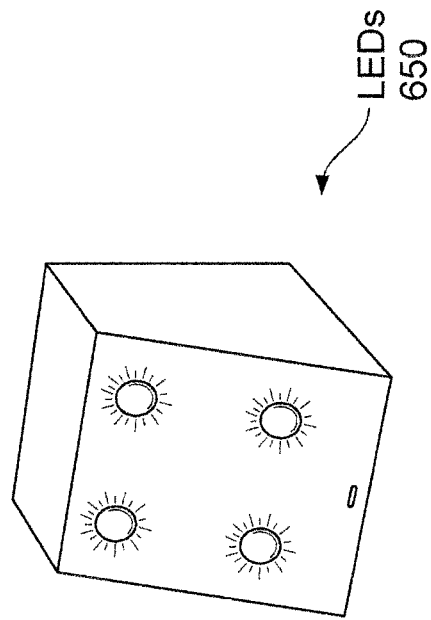
FIGS. 8A-B illustrate LED lights for an EEG system for SEPs in accordance with some embodiments.
Figure 8A:
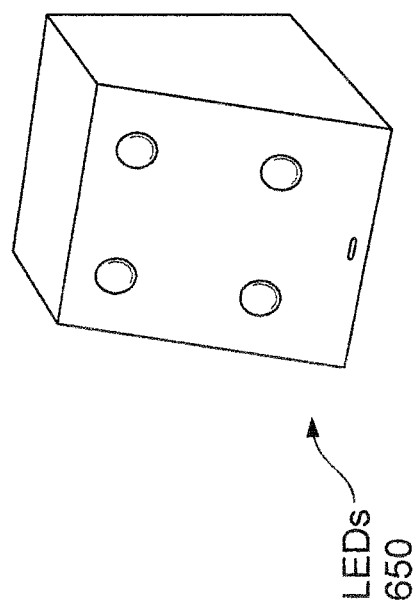

FIGS. 8A-B illustrate LED lights for an EEG system for SEPs in accordance with some embodiments. As shown, FIG. 8A illustrates the LED lights 650 in which all four LED lights are turned off (e.g., not flashed on). As shown, FIG. 8B illustrates the LED lights 650 in which all four LED lights are turned on (e.g., flashed on). As shown, the LED lights 650 are mounted in a box shaped apparatus, which, for example, can flash in patterns that represent commands to a user. In some embodiments, each of the four separate LED lights of the LED lights system 650 can flash on/off independently. In some embodiments, the LED lights of the LED lights system 650 flash at distinct fixed frequencies. In some embodiments, the LED lights of the LED lights system 650 flash at variable frequencies in a fixed pattern. In some embodiments, each of the four LED lights flashes at a different frequency. In some embodiments, the frequencies of each of the LED lights are separated by 1 or 2 Hz (e.g., the four LED lights can be set at the following frequencies: 9 Hz, 10 Hz, 11 Hz, and 12 Hz, or other frequencies, such as in the range of 8 Hz to 20 Hz or some other frequency range for which SEPs can effectively be detected). In some embodiments, fewer than four or more than four LEDs are included in the LED lights system 650. In some embodiments, the flashing pattern is controlled by the controller 620 (e.g., controlling the frequency of the flashing using an FPGA controller, such as a Xilinx FPGA chip that executes Verilog code).

Figure 9A:
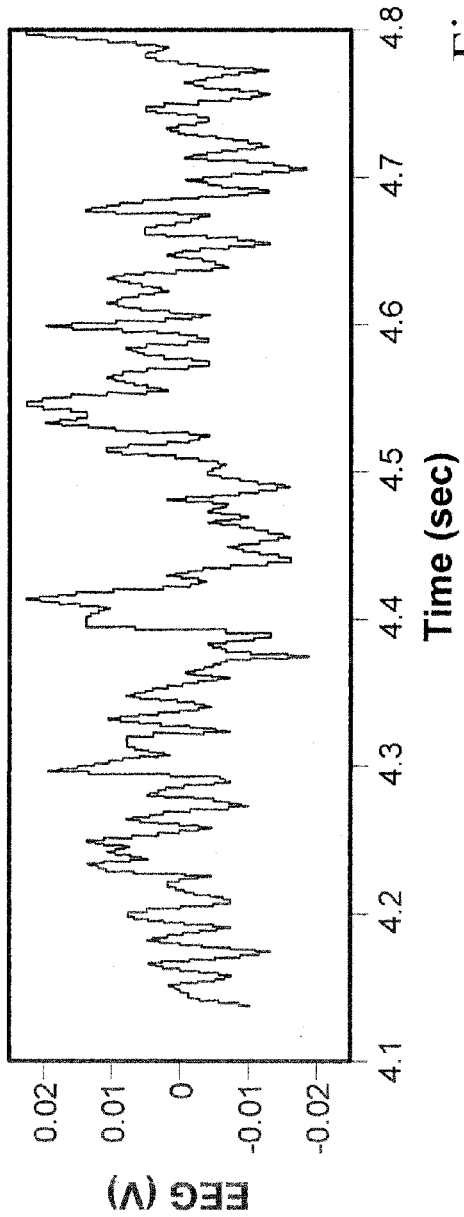
FIGS. 9A-B are charts illustrating EEG data and light control signal data for an EEG system for SEPs in accordance with some embodiments.
Figure 9B:
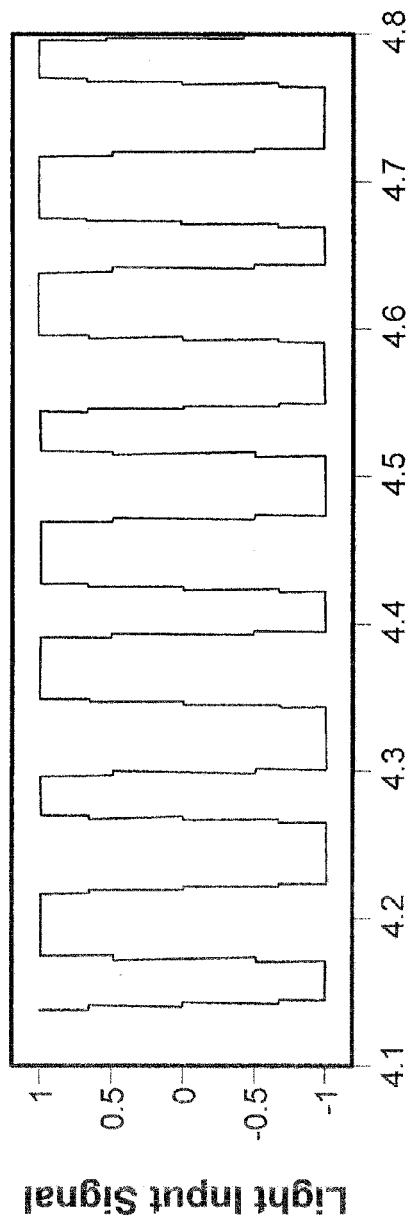

FIGS. 9A-B are charts illustrating EEG data and light control signal data for an EEG system for SEPs in accordance with some embodiments. FIG. 9A illustrates measured EEG signals (in Volts (V)) relative to time (in seconds). FIG. 9B illustrates the light input signal (in Hertz (Hz)) (e.g., flashing light events) relative to time (in seconds). As shown, the light input signal is a square wave of a fixed frequency.

Figure 10:
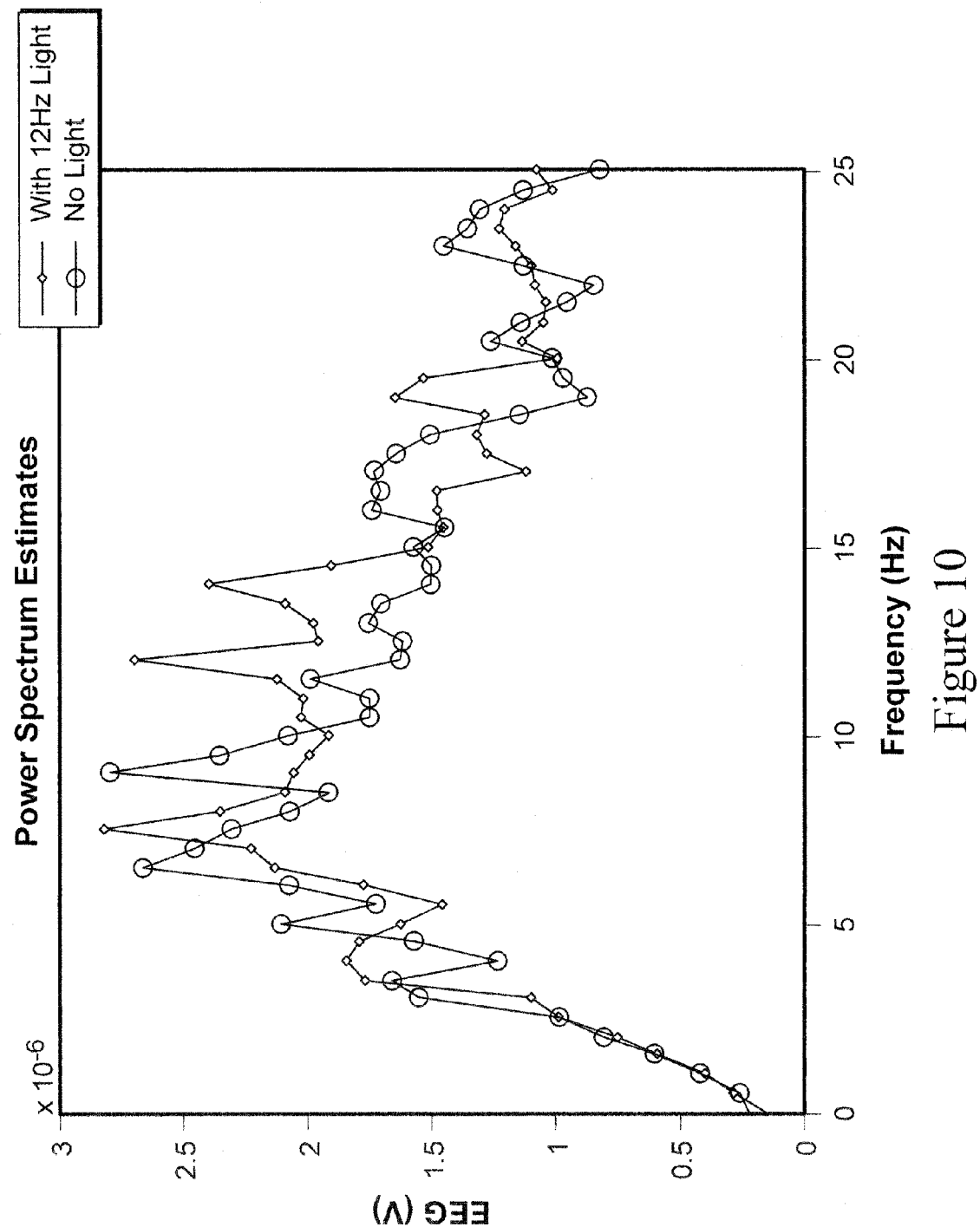
FIG. 10 is a power spectrum chart for sample EEG data.

FIG. 10 is a power spectrum chart for sample EEG data. In particular, FIG. 10 illustrates measured EEG signals (in V) relative to frequency (in Hz), in which there are two measurements depicted, a first measured EEG signal for which no light events are present, and a second measured signal for which 12 Hz light events occurred and the user was looking at a light that flashed on and off at a fixed frequency of 12 Hz. As illustrated in this example shown in FIG. 10 and as discussed above, it is difficult to determine if the increased power at 12 Hz is due to looking at a 12 Hz light, or if it is irrelevant noise.

Figure 11:
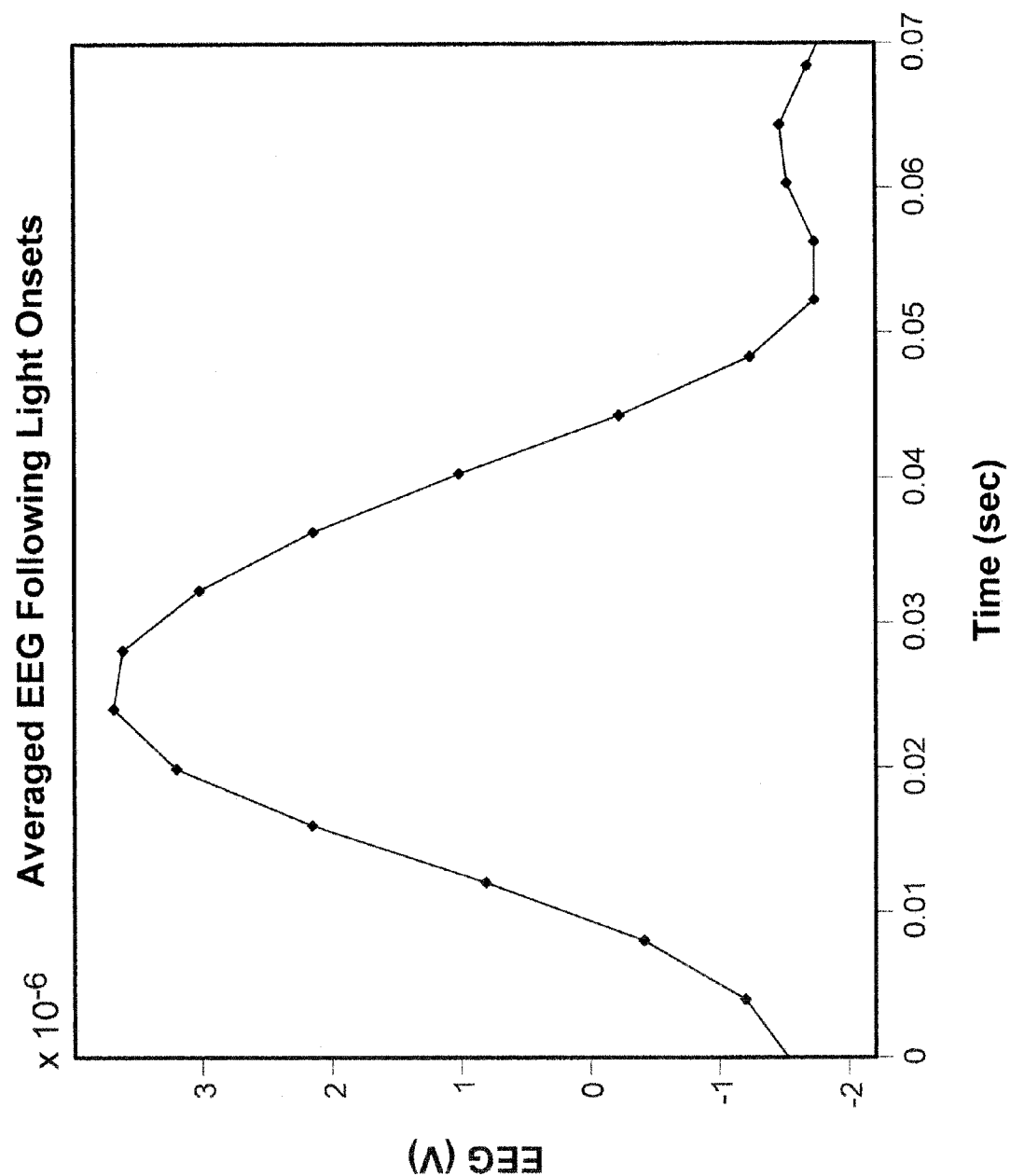
FIG. 11 is a chart illustrating averaged EEG data following light onsets for an EEG system for SEPs in accordance with some embodiments.

FIG. 11 is a chart illustrating averaged EEG data following light onsets for an EEG system for SEPs in accordance with some embodiments. In particular, FIG. 11 illustrates an averaged EEG signal following light onsets (e.g., a 12 Hz flashing light event) in which the average of the time series of data is time-locked to the 12 Hz flashing light. As shown, the flash-locked average signal provides a signal shape that can be recognized to detect that the light is being attended (e.g., observed by the user), such that an SEP is effectively detected (e.g., using a threshold comparison and/or a signature signal comparison, as discussed herein).

Figure 12:
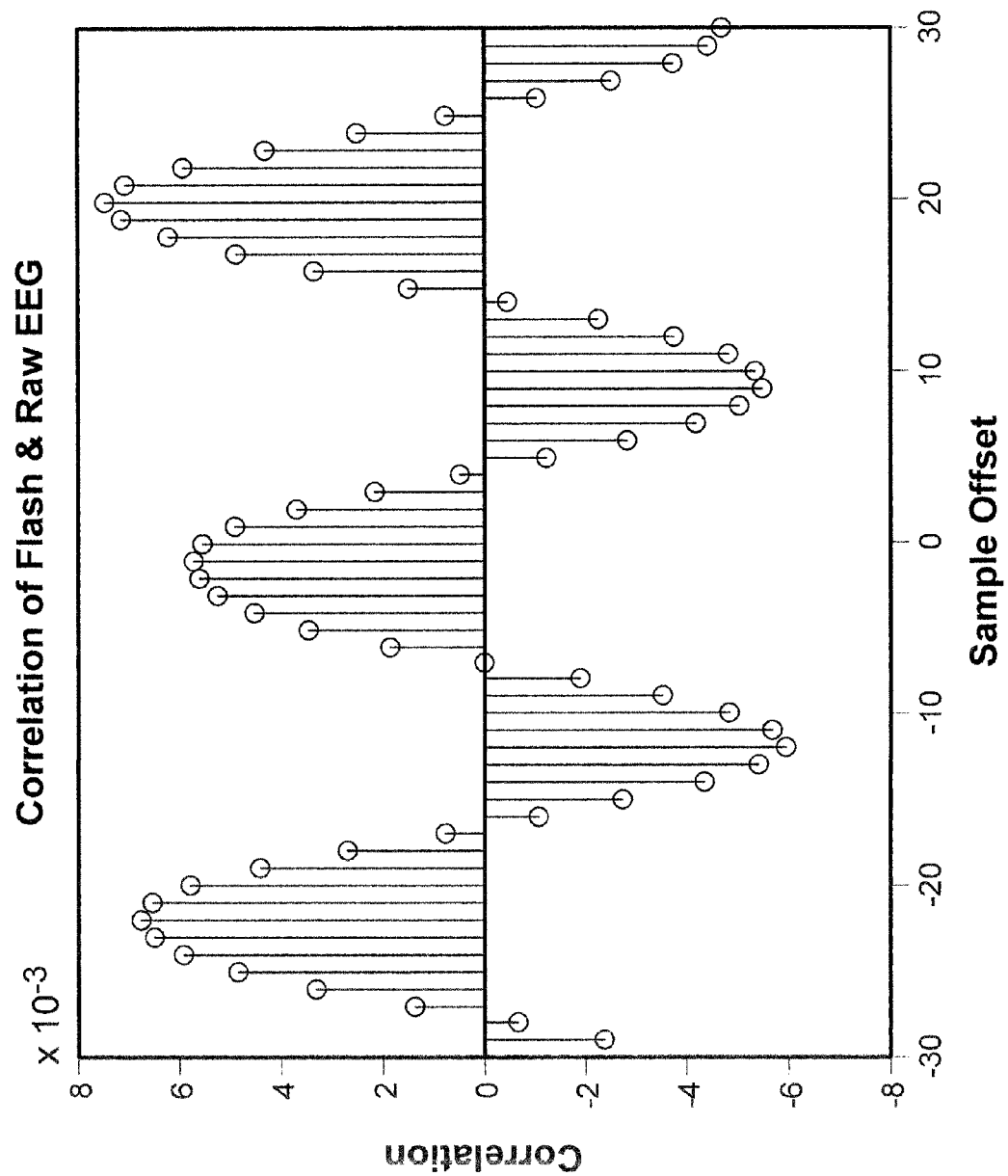
FIG. 12 is a chart illustrating a correlation of light flash and raw EEG data for an EEG system for SEPs in accordance with some embodiments.

FIG. 12 is a chart illustrating a correlation of flash and raw EEG data for an EEG system for SEPs in accordance with some embodiments. In particular, FIG. 12 illustrates a correlation analysis between averaged EEG signals (e.g., flash-locked average signals) and flashing light events (e.g., light flashes). At each discrete point in time, the measured EEG signals and the measured light signals are multiplied together. All of these results are averaged together to form a correlation number. In some embodiments, the analysis is repeated using time offsets between the EEG data and the light signal data (e.g., 30 ms). The result is a characteristic shape that can be used to determine that the light is being attended (e.g., observed by the user), such that an SEP is effectively detected.

Figure 13:
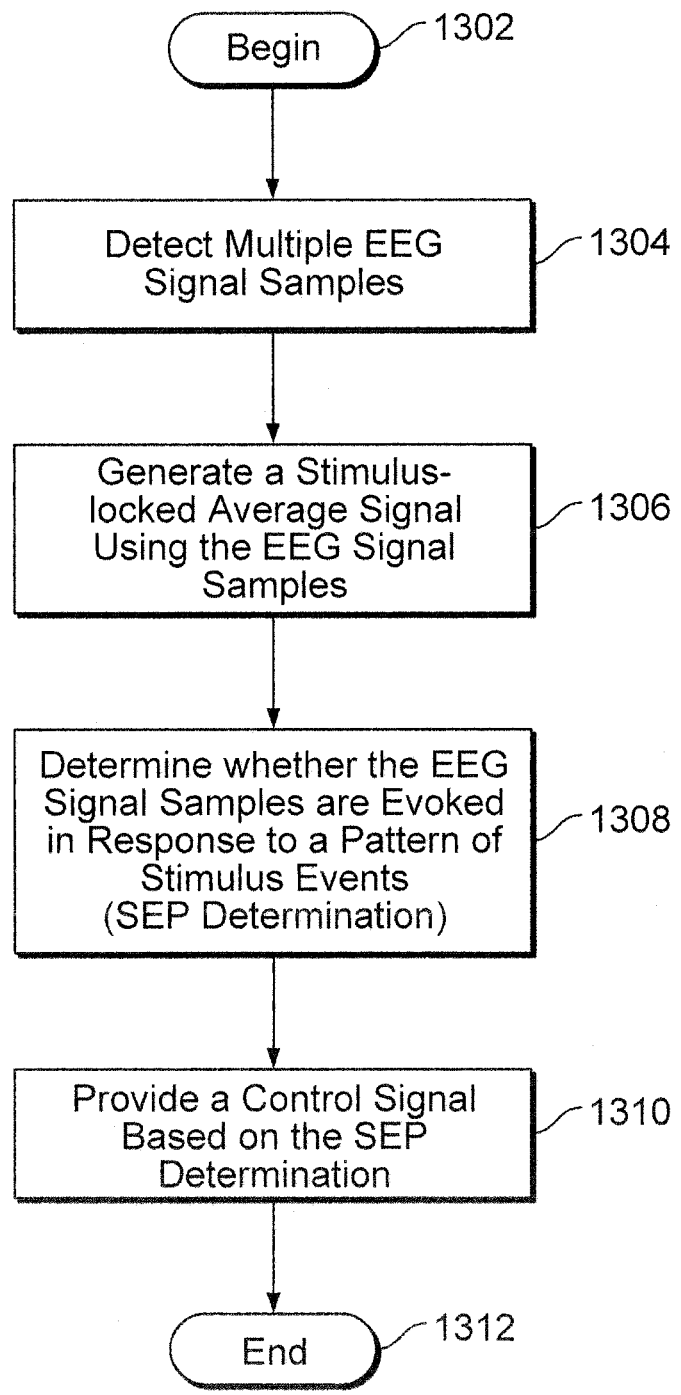
FIG. 13 is a flow chart for an EEG system for SEPs in accordance with some embodiments.

FIG. 13 is a flow chart for an EEG system for SEPs in accordance with some embodiments. At 1302, the process begins. At 1304, multiple EEG signal samples are detected. At 1306, a stimulus-locked average signal is generated using the EEG signal samples. In some embodiments, an average of the EEG signal is determined that is time-locked to the light onset and/or offset event(s). For example, for a specified period (e.g., 50 ms) after a light onset the EEG signal is recorded, and such recording is performed after each of one or more light onsets. The resulting 50 ms EEG segments are then averaged together to provided the averaging signal. At 1308, whether the EEG signal samples are evoked in response to a pattern of stimulus events (e.g., an SEP determination, such as in response to a visual event) is determined. For example, a characteristic shape of the stimulus-locked average signal can be detected using various techniques including comparing to a threshold at some delay from the onset, integrating the averaged EEG signal over some time period and comparing that result to a threshold, or creating a classifier that distinguishes if the light is being attended. As another example, a prototype of an ideal average (e.g., when a light is being attended) can be constructed and multiplied by the actual average. A high value result will indicate an attended light. The prototype can be constructed in a variety of ways, including computing EEG averages when a user is known to be looking at the light, or constructing an auto-regression model of EEG data when a user is known to be looking at the light, and using the coefficients of that auto-regression model as the data elements of the prototype. At 1310, a control signal is provided based on the SEP determination. At 1312, the process is completed.

Figure 14:
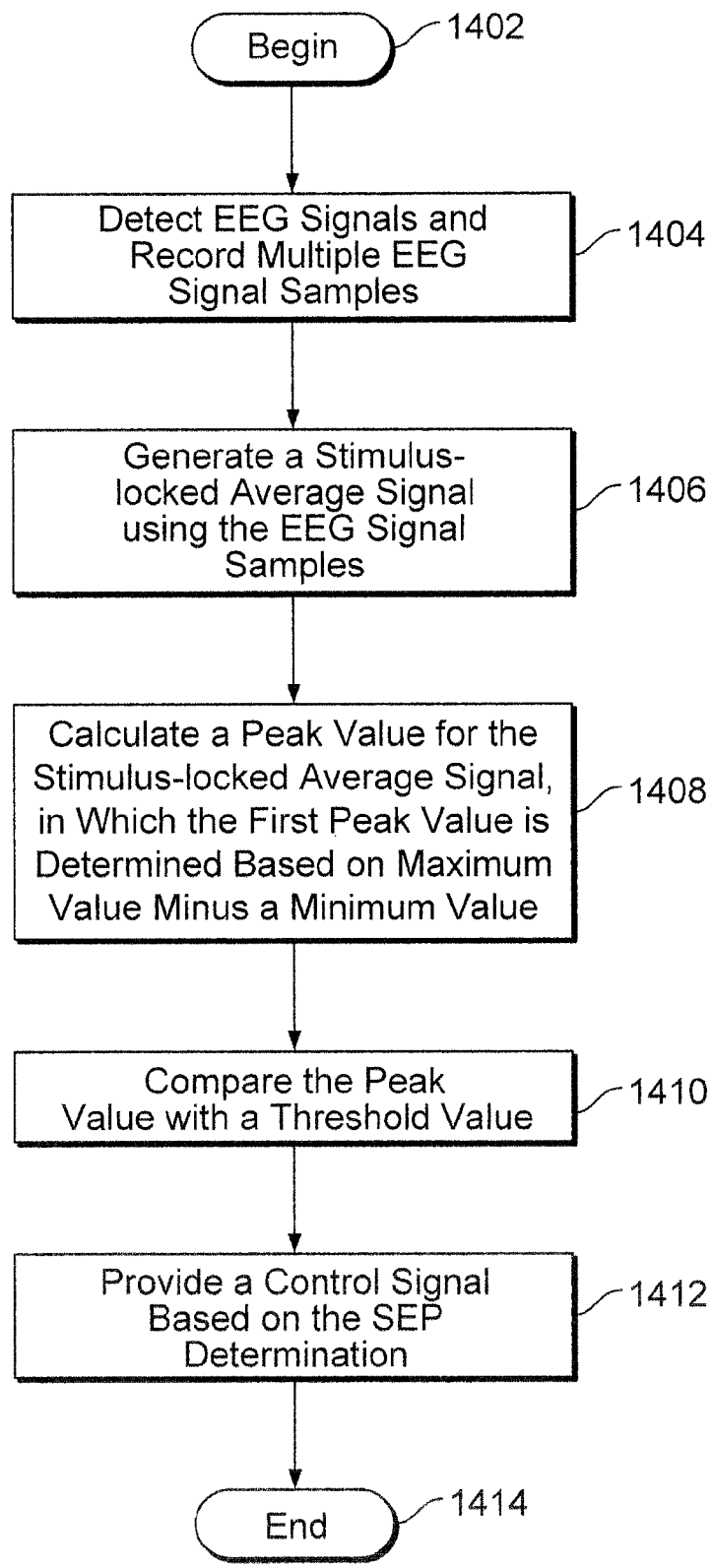
FIG. 14 is another flow chart for an EEG system for SEPs in accordance with some embodiments.

FIG. 14 is another flow chart for an EEG system for SEPs in accordance with some embodiments. At 1402, the process begins. At 1404, multiple EEG signal samples are detected and recorded (e.g., stored). At 1406, a stimulus-locked average signal is generated using the EEG signal samples. At

1408, a peak value for the stimulus-locked average signal is calculated, in which the first peak value is determined based on maximum value minus a minimum value of the averaged signal. At 1410, the peak value is compared with a threshold value. For example, if the user experienced the stimulus evoked event (e.g., was looking at the flashing light), then the averaged EEG signal will generally include a noticeable peak shortly after the flash onsets (e.g., after an offset of about 30 ms to 50 ms for such SEPs). As a result, a threshold (e.g., signature signal) can be set up to determine if a peak exists. In some embodiments, the system is trained based on testing with a particular user, and the threshold values (or, in some embodiments, signal signatures) are generated based on the training. In some embodiments, the EEG signal samples are correlated with the pattern of stimulus events using a time delay offset (e.g., 30 ms to 50 ms) to determine whether the EEG signal samples are evoked in response to a pattern of stimulus events (e.g., an SEP determination, such as in response to a visual event). At 1412, a control signal is provided based on the SEP determination. At 1414, the process is completed.

Figure 15:
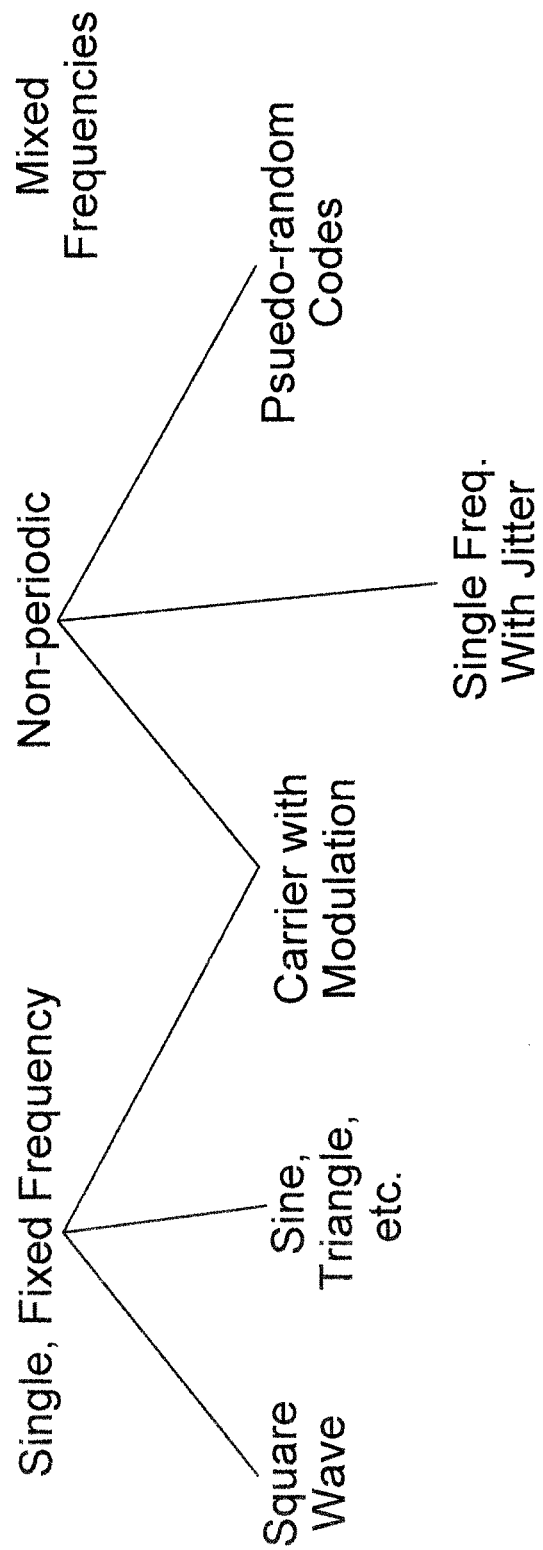
FIG. 15 is a diagram illustrating different stimulus types in accordance with some embodiments.

FIG. 15 is a diagram illustrating different stimulus frequency types in accordance with some embodiments. As shown, a stimulus frequency for the light input signal can be a single, fixed frequency, such as a square wave, a sign or triangle wave, or a carrier with modulation. In some embodiments, a mixed frequency stimulus is used, in which a mixed frequency stimulus is, for example, a combination of two or more fixed frequencies added together. In some embodiments, various other types of non-periodic signals are used and are matched with time domain analysis. For example, a carrier wave with modulation would be similar to an FM radio signal with a large sine-wave component at a fixed frequency combined with a different smaller signal. As another example, a single-frequency stimulus can be adjusted by adding some variation in the frequency. As will be appreciated, there are also many ways to construct pseudo-random codes, such as CDMA codes used in cell phone networks.

Figure 16:
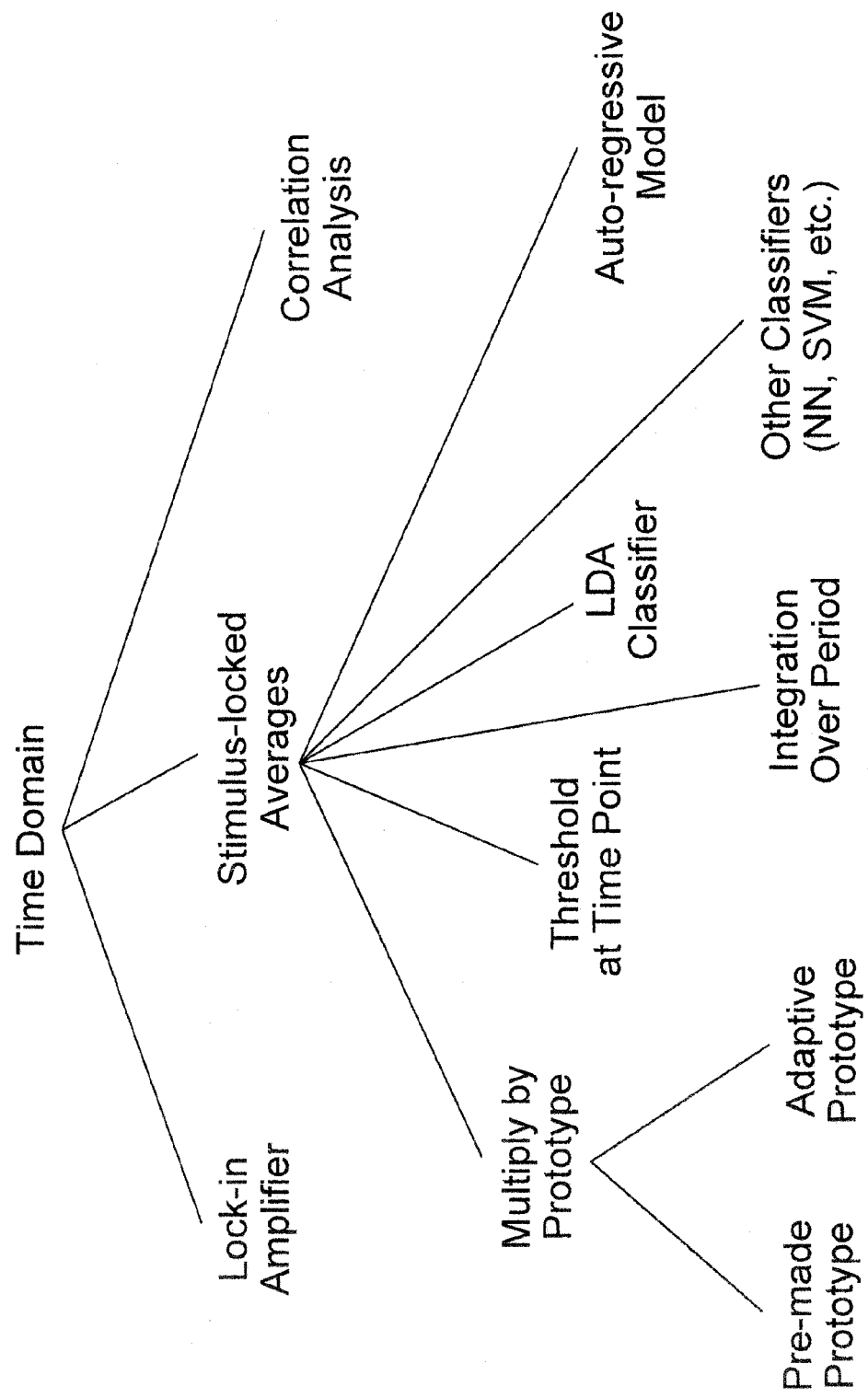
FIG. 16 is a diagram illustrating time domain algorithms in accordance with some embodiments.

FIG. 16 is a diagram illustrating time domain algorithms in accordance with some embodiments. In some embodiments, time domain classifier techniques use the EEG signal without a conversion to the frequency domain. For example, one approach that can be used is to multiply the EEG signal by sine waves of the same frequency as the flashing light. If the sine wave has the correct frequency and phase, the output will have a relatively large amplitude. The absolute value of such an output will be relatively high, compared with incorrect sine waves. As another example, a correlation analysis can be used that would multiply each point of the EEG data with each point of the light intensity data (e.g., after the means are subtracted away). If there is no correlation between the two vectors of data, the output will be zero. The correlation can also be computed between the light intensity data and a delayed version of the EEG (e.g., using an appropriate offset, such as 30 ms to 50 ms). At some delay, the correlation will typically be strong for a light that is being attended. Various embodiments of stimulus-locked averaging techniques are further described below.

FIG. 17 is a chart illustrating an example of four stimulus-locked averages in accordance with some embodiments. One of the averages has developed a characteristic shape, and the other averages are relatively flat.

FIG. 18 is a chart illustrating an example for generating a flash-locked average signal in accordance with some embodiments. As shown in FIG. 18, an EEG signal from a user looking at a flashing light and a signal that is used to control the light are both measured. Segments of the EEG signal of a fixed length (e.g., 100 ms) that follow the light onsets are first recorded. The recorded data is then averaged together such that the first EEG data points following light onsets are averaged together, then all the second data points that follow light onsets are averaged together, then the third data points that follow light onsets are averaged together, and so forth. The result provides an average waveform of the same length as the recorded segments. For example, if the user looked at the light, then the averaged waveform will include a characteristic shape (e.g., a positive deflection in EEG voltage about 30 ms to 50 ms after the light onset time). This characteristic shape can be detected in a variety of ways. If the user did not look at the light the averaged waveform will be mostly flat. In some embodiments, this technique is similarly used for generating a stimulus-locked average signal. In some embodiments, the measured EEG signals include involuntary EEG signal responses. In some embodiments, the measured EEG signals also include voluntary EEG signal responses, such as intensity or focus related EEG signal responses (e.g., the strength of the EEG signal can be altered by the way in which (such as a periphery versus a direct focus) or the intensity with which a user looks at a flashing light(s)).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
 a processor configured to:
  generate a stimulus-locked average signal of a plurality of EEG signal samples; and
  determine whether the plurality of EEG signal samples are evoked in response to a pattern of stimulus events, wherein:
   the determination of whether the plurality of EEG signal samples are evoked in response to a pattern of stimulus events includes multiplying the stimulus-locked average by a prototype average that adapts to a user's EEG signals; or
   the determination of whether the plurality of EEG signal samples are evoked in response to a pattern of stimulus events includes integrating the EEG signal data to generate a result, and comparing the result to a threshold; or
   the determination of whether the plurality of EEG signal samples are evoked in response to a pattern of stimulus events is performed using a time domain classifier; and
 a memory coupled to the processor and configured to provide the processor with instructions.

2. The system recited in claim 1, wherein the pattern of stimulus events is provided by a plurality of light sources of the system, the light sources emitting light flashes periodically at a fixed frequency.

3. The system recited in claim 1, wherein the pattern of stimulus events is provided by a plurality of light sources of the system, the light sources emitting light flashes periodically, including a first light source emitting light flashes a first fixed frequency and a second light source emitting light flashes at a second fixed frequency.

4. The system recited in claim 1, wherein the pattern of stimulus events is provided by a light source of the system, the light source emitting light flashes periodically at a plurality of frequencies, including a first light flash at a first frequency and a second light flash at a second frequency.

5. The system recited in claim 1, wherein the pattern of stimulus events is provided by a plurality of light sources of the system, the light sources emitting light flashes at non-periodic frequencies.

6. The system recited in claim 1, wherein the pattern of stimulus events is provided by a plurality of light sources of the system, the pattern of stimulus events including one or more of the following: a pattern of visual stimulus events, a pattern of audio stimulus events, and a pattern of tactile stimulus events.

7. The system recited in claim 1, wherein the pattern of stimulus events is provided by a plurality of light sources of the system, each light source providing independent flashing light events.

8. The system recited in claim 1, wherein the generating of the stimulus-locked average signal includes generating the stimulus-locked average signal including a flash-locked average signal.

9. The system recited in claim 1, wherein the determination of whether the plurality of EEG signal samples are evoked in response to a pattern of stimulus events is performed in real-time.

10. The system recited in claim 1, wherein the processor is further configured to:
determine whether a user of the system is looking at a first light source.

11. The system recited in claim 1, wherein the processor is further configured to:
correlate the plurality of EEG signal samples with the pattern of stimulus events using a time offset based on stimulus timing.

12. The system recited in claim 1, further comprising:
a plurality of electrodes including an active EEG electrode and a reference EEG electrode, wherein the plurality of electrodes detect the plurality of EEG signal samples.

13. The system recited in claim 1, wherein the processor is further configured to:
provide a control signal based on a determination of whether the plurality of EEG signal samples are evoked in response to the pattern of stimulus events.

14. The system recited in claim 1, wherein the processor is further configured to:
provide a control signal to a device based on a determination of whether the plurality of EEG signal samples are evoked in response to the pattern of stimulus events, wherein the device includes one or more of the following: an entertainment system, an educational system, a medical system, an automobile system, and a computer executing an application.

15. A method, comprising:
measuring a plurality of EEG signal samples using a bio-signal sensor;
generating a stimulus-locked average signal using the plurality of EEG signal samples using a processor; and
determining whether the plurality of EEG signal samples are evoked in response to a stimulus using the processor, wherein:
the determination of whether the plurality of EEG signal samples are evoked in response to a pattern of stimulus events includes multiplying the stimulus-locked average by a prototype average that adapts to a user's EEG signals; or
the determination of whether the plurality of EEG signal samples are evoked in response to a pattern of stimulus events includes integrating the EEG signal data to generate a result, and comparing the result to a threshold; or
the determination of whether the plurality of EEG signal samples are evoked in response to a pattern of stimulus events is performed using a time domain classifier.

16. A computer program product, the computer program product being embodied in a non-transitory computer readable storage medium and comprising computer instructions for:
recording a plurality of EEG signal samples;
generating a stimulus-locked average signal using the plurality of EEG signal samples; and
determining whether the plurality of EEG signal samples are evoked in response to a stimulus, wherein:
the determination of whether the plurality of EEG signal samples are evoked in response to a pattern of stimulus events includes multiplying the stimulus-locked average by a prototype average that adapts to a user's EEG signals; or
the determination of whether the plurality of EEG signal samples are evoked in response to a pattern of stimulus events includes integrating the EEG signal data to generate a result, and comparing the result to a threshold; or
the determination of whether the plurality of EEG signal samples are evoked in response to a pattern of stimulus events is performed using a time domain classifier.

\* \* \* \* \*